(12) United States Patent  
Glaser

(10) Patent No.: US 7,473,266 B2  
(45) Date of Patent: Jan. 6, 2009

(54) COLLET-BASED DELIVERY SYSTEM

(75) Inventor: Erik N. Glaser, S. Dartmouth, MA (US)

(73) Assignee: NMT Medical, Inc., Boston, MA (US)

( * ) Notice: Subject to any disclaimer, the term of this patent is extended or adjusted under 35 U.S.C. 154(b) by 459 days.

(21) Appl. No.: 10/389,478

(22) Filed: Mar. 14, 2003

(65) Prior Publication Data

US 2004/0181256 A1    Sep. 16, 2004

(51) Int. Cl.
    *A61B 17/08*    (2006.01)
(52) U.S. Cl. .................. 606/213; 606/206; 606/200
(58) Field of Classification Search ............ 606/139, 606/142, 206, 205, 207, 213, 200; 623/1–23; 81/453
    See application file for complete search history.

(56) References Cited

U.S. PATENT DOCUMENTS

| | | | | |
|---|---|---|---|---|
| 1,889,330 A | * | 11/1932 | Humes et al. ................. 81/453 |
| 2,625,967 A | * | 1/1953 | Stull ......................... 81/57.42 |
| 3,874,388 A | | 4/1975 | King et al. ................ 128/334 R |
| 4,007,743 A | | 2/1977 | Blake ....................... 128/334 R |
| 4,422,654 A | | 12/1983 | Grunig ........................... 279/4 |
| 4,477,105 A | | 10/1984 | Wittman et al. ................ 285/18 |
| 4,836,204 A | | 6/1989 | Landymore et al. ...... 128/334 R |
| 4,985,014 A | | 1/1991 | Orejola ......................... 600/16 |
| 5,030,199 A | | 7/1991 | Barwick et al. ................ 600/29 |
| 5,041,129 A | | 8/1991 | Hayhurst et al. ............. 606/232 |
| 5,042,976 A | | 8/1991 | Ishitsu et al. .................. 604/96 |
| 5,057,114 A | | 10/1991 | Wittich et al. ............... 606/127 |
| 5,073,166 A | | 12/1991 | Parks et al. .................... 609/93 |
| 5,108,420 A | | 4/1992 | Marks .......................... 606/213 |
| 5,112,310 A | | 5/1992 | Grobe ......................... 604/175 |
| 5,186,567 A | | 2/1993 | Evenson et al. ................. 403/7 |
| 5,190,528 A | | 3/1993 | Fonger et al. ................ 604/171 |
| 5,192,301 A | | 3/1993 | Kamiya et al. .............. 606/213 |
| 5,211,515 A | | 5/1993 | Hirabayashi ................ 409/230 |
| 5,217,484 A | * | 6/1993 | Marks ......................... 606/200 |
| 5,222,973 A | * | 6/1993 | Sharpe et al. ............... 606/206 |
| 5,284,488 A | | 2/1994 | Sideris ........................ 606/213 |
| 5,304,195 A | * | 4/1994 | Twyford, Jr. et al. ......... 606/191 |

(Continued)

FOREIGN PATENT DOCUMENTS

| | | |
|---|---|---|
| EP | 1222897 | 7/2002 |
| WO | WO 98/07375 | 2/1998 |
| WO | WO 99/18862 | 4/1999 |
| WO | WO 99/18864 | 4/1999 |
| WO | WO 99/18870 | 4/1999 |
| WO | WO 99/18871 | 4/1999 |
| WO | WO 01/78596 | 10/2001 |
| WO | WO 03/077733 A2 | 9/2003 |

OTHER PUBLICATIONS

Mechanical Fingers—Product Description, *Small Parts Inc.: Engineering Findings*, p. 297, (1998).

(Continued)

*Primary Examiner*—Darwin P Erezo
(74) *Attorney, Agent, or Firm*—K & L Gates LLP

(57) ABSTRACT

A delivery device for implanting a medical device including a flexible elongate member that is sized and shaped to fit within a body vessel. A collet is located at a first end of the flexible elongate member and has at least two arms being movable between a first open state and a second collapsed state. The arms form an inner chamber when in the collapsed state. The elongate member substantially surrounds the collet in a first position and is substantially separated from the collet in a second position thereby moving the arms between the closed state and the open state.

12 Claims, 4 Drawing Sheets

U.S. PATENT DOCUMENTS

| | | | | |
|---|---|---|---|---|
| 5,308,357 | A * | 5/1994 | Lichtman | 606/205 |
| 5,312,341 | A | 5/1994 | Turi | 604/96 |
| 5,318,589 | A * | 6/1994 | Lichtman | 606/205 |
| 5,334,217 | A | 8/1994 | Das | 606/213 |
| 5,350,397 | A * | 9/1994 | Palermo et al. | 606/200 |
| 5,357,979 | A | 10/1994 | Imran | 128/772 |
| 5,403,338 | A | 4/1995 | Milo | 606/184 |
| 5,425,744 | A | 6/1995 | Fagan et al. | 606/213 |
| 5,431,416 | A | 7/1995 | Thornton | 279/4.08 |
| 5,433,727 | A | 7/1995 | Sideris | 606/213 |
| 5,443,464 | A | 8/1995 | Russell et al. | 606/54 |
| 5,451,235 | A | 9/1995 | Lock et al. | 606/213 |
| 5,507,811 | A | 4/1996 | Koike et al. | 623/11 |
| 5,540,712 | A | 7/1996 | Kleshinski et al. | 606/198 |
| 5,545,138 | A | 8/1996 | Fugoso et al. | 604/102 |
| 5,577,299 | A | 11/1996 | Thompson et al. | 24/131 C |
| 5,578,045 | A | 11/1996 | Das | 606/151 |
| 5,620,461 | A | 4/1997 | Muijs Van De Moer et al. | 606/213 |
| 5,626,604 | A | 5/1997 | Cottone, Jr. | 606/198 |
| 5,634,936 | A | 6/1997 | Linden et al. | 606/213 |
| 5,638,827 | A * | 6/1997 | Palmer et al. | 600/564 |
| 5,665,100 | A * | 9/1997 | Yoon | 606/170 |
| 5,683,411 | A | 11/1997 | Kavteladze et al. | 606/200 |
| 5,702,421 | A | 12/1997 | Schneidt | 606/213 |
| 5,709,707 | A | 1/1998 | Lock et al. | 606/213 |
| 5,713,952 | A | 2/1998 | Vanney et al. | 623/2 |
| 5,720,754 | A | 2/1998 | Middleman et al. | 606/127 |
| 5,725,552 | A | 3/1998 | Kotula et al. | 606/213 |
| 5,733,294 | A | 3/1998 | Forber et al. | 606/151 |
| 5,741,297 | A | 4/1998 | Simon | 606/213 |
| 5,746,765 | A | 5/1998 | Kleshinski et al. | 606/198 |
| 5,776,075 | A * | 7/1998 | Palmer | 600/564 |
| 5,776,162 | A | 7/1998 | Kleshinski | 606/198 |
| 5,797,958 | A * | 8/1998 | Yoon | 606/207 |
| 5,800,516 | A | 9/1998 | Fine et al. | 523/1 |
| 5,807,405 | A | 9/1998 | Vanney et al. | 623/112 |
| 5,810,884 | A | 9/1998 | Kim | 606/213 |
| 5,853,422 | A | 12/1998 | Huebsch et al. | 606/213 |
| 5,861,003 | A | 1/1999 | Latson et al. | 606/213 |
| 5,868,753 | A | 2/1999 | Schatz | 606/108 |
| 5,876,437 | A | 3/1999 | Vanney et al. | 623/2 |
| 5,879,366 | A | 3/1999 | Shaw et al. | 606/213 |
| 5,888,200 | A | 3/1999 | Walen | 606/167 |
| 5,891,130 | A * | 4/1999 | Palermo et al. | 606/1 |
| 5,895,391 | A * | 4/1999 | Farnholtz | 606/108 |
| 5,895,404 | A | 4/1999 | Ruiz | 606/185 |
| 5,902,317 | A | 5/1999 | Kleshinski et al. | 606/198 |
| 5,904,695 | A | 5/1999 | Krueger | 606/151 |
| 5,904,703 | A | 5/1999 | Gilson | 606/213 |
| 5,919,200 | A | 7/1999 | Stambaugh et al. | 606/159 |
| 5,928,250 | A | 7/1999 | Koike et al. | 606/139 |
| 5,944,738 | A | 8/1999 | Amplatz et al. | 606/213 |
| 5,957,976 | A | 9/1999 | Vanney et al. | 623/2 |
| 5,976,174 | A | 11/1999 | Ruiz | 606/213 |
| 5,989,242 | A * | 11/1999 | Saadat et al. | 606/1 |
| 5,993,474 | A * | 11/1999 | Ouchi | 606/206 |
| 5,993,475 | A | 11/1999 | Lin et al. | 606/213 |
| 6,007,558 | A | 12/1999 | Ravenscroft et al. | 606/200 |
| 6,024,756 | A | 2/2000 | Huebsch et al. | 606/213 |
| 6,030,007 | A | 2/2000 | Bassily et al. | 289/1.5 |
| 6,030,405 | A | 2/2000 | Zarbatany et al. | 606/191 |
| 6,056,760 | A | 5/2000 | Koike et al. | 606/148 |
| 6,077,291 | A | 6/2000 | Das | 606/213 |
| 6,080,182 | A | 6/2000 | Shaw et al. | 606/213 |
| 6,086,610 | A | 7/2000 | Duerig et al. | 623/1 |
| 6,113,609 | A | 9/2000 | Adams | 606/139 |
| 6,117,143 | A | 9/2000 | Hynes et al. | 606/130 |
| 6,117,159 | A | 9/2000 | Huebsch et al. | 606/213 |
| 6,129,755 | A | 10/2000 | Mathis et al. | 623/1.15 |
| 6,146,325 | A | 11/2000 | Lewis et al. | 600/16 |
| 6,149,664 | A | 11/2000 | Kurz | 606/194 |
| 6,171,329 | B1 | 1/2001 | Shaw et al. | 606/213 |
| 6,174,322 | B1 | 1/2001 | Schneidt | 606/213 |
| 6,190,373 | B1 * | 2/2001 | Palermo et al. | 606/1 |
| 6,206,907 | B1 | 3/2001 | Marino et al. | 606/215 |
| 6,209,886 | B1 | 4/2001 | Estes et al. | 279/50 |
| 6,214,029 | B1 | 4/2001 | Thill et al. | 606/213 |
| 6,221,092 | B1 | 4/2001 | Koike et al. | 606/213 |
| 6,261,916 | B1 * | 7/2001 | Re et al. | 606/108 |
| 6,270,515 | B1 | 8/2001 | Linden et al. | 606/213 |
| 6,290,674 | B1 | 9/2001 | Roue et al. | 604/107 |
| 6,296,622 | B1 | 10/2001 | Kurz et al. | 604/93.01 |
| 6,312,446 | B1 | 11/2001 | Huebsch et al. | 606/213 |
| 6,322,548 | B1 | 11/2001 | Payne et al. | 604/500 |
| 6,342,064 | B1 | 1/2002 | Koike et al. | 606/213 |
| 6,346,074 | B1 | 2/2002 | Roth | 600/121 |
| 6,352,531 | B1 | 3/2002 | O'Connor et al. | 606/15 |
| 6,355,052 | B1 | 3/2002 | Neuss et al. | 606/213 |
| 6,368,330 | B1 | 4/2002 | Hynes et al. | 606/130 |
| 6,375,671 | B1 | 4/2002 | Kobayashi et al. | 606/213 |
| 6,379,368 | B1 | 4/2002 | Corcoran et al. | 606/153 |
| 6,387,104 | B1 | 5/2002 | Pugsley, Jr. et al. | 606/139 |
| 6,402,772 | B1 | 6/2002 | Amplatz et al. | 606/200 |
| 6,415,693 | B1 * | 7/2002 | Simon et al. | 81/453 |
| 6,440,152 | B1 | 8/2002 | Gainor et al. | 606/213 |
| 6,482,224 | B1 | 11/2002 | Michler et al. | 606/219 |
| 6,494,888 | B1 | 12/2002 | Laufer et al. | 606/153 |
| 6,508,825 | B1 * | 1/2003 | Selmon et al. | 606/198 |
| 6,551,344 | B2 | 4/2003 | Thill | 606/213 |
| 6,596,013 | B2 | 7/2003 | Yang et al. | 606/215 |
| 6,623,508 | B2 | 9/2003 | Shaw et al. | 606/213 |
| 6,623,518 | B2 | 9/2003 | Thompson et al. | 623/1.11 |
| 6,673,100 | B2 * | 1/2004 | Diaz et al. | 623/1.11 |
| 6,849,081 | B2 * | 2/2005 | Sepetka et al. | 606/213 |
| 7,344,553 | B2 * | 3/2008 | Opolski et al. | 606/207 |
| 2001/0037129 | A1 | 11/2001 | Thill | 606/213 |
| 2002/0010481 | A1 | 1/2002 | Jayaraman et al. | 606/151 |
| 2002/0019648 | A1 | 2/2002 | Akerfeldt et al. | 606/213 |
| 2002/0026208 | A1 | 2/2002 | Roe et al. | 606/190 |
| 2002/0052572 | A1 | 5/2002 | Franco et al. | 604/8 |
| 2002/0077555 | A1 | 6/2002 | Schwartz et al. | 600/486 |
| 2002/0096183 | A1 | 7/2002 | Stevens et al. | 128/898 |
| 2002/0099389 | A1 | 7/2002 | Michler et al. | 606/139 |
| 2002/0107531 | A1 | 8/2002 | Schreck et al. | 606/142 |
| 2002/0120323 | A1 | 8/2002 | Thompson et al. | 623/1.11 |
| 2002/0128680 | A1 | 9/2002 | Pavlovic | 606/200 |
| 2002/0183786 | A1 | 12/2002 | Girton | 606/213 |
| 2002/0183787 | A1 | 12/2002 | Wahr et al. | 606/213 |
| 2003/0028213 | A1 | 2/2003 | Thill et al. | 606/200 |
| 2003/0045893 | A1 | 3/2003 | Ginn | 606/151 |
| 2003/0050665 | A1 | 3/2003 | Ginn | 505/215 |
| 2003/0059640 | A1 | 3/2003 | Marton et al. | 428/544 |
| 2003/0100920 | A1 | 5/2003 | Akin et al. | 606/213 |
| 2003/0139819 | A1 | 7/2003 | Beer et al. | 623/23 |
| 2003/0181945 | A1 | 9/2003 | Opolski | |
| 2003/0195530 | A1 | 10/2003 | Thill | 606/151 |
| 2003/0208232 | A1 | 11/2003 | Blaeser et al. | 606/213 |

OTHER PUBLICATIONS

"Trans-spetal Catheterization for Radiofrequncey Catheter Ablation of Cardiac Arryhythmias. Results and Safety of a Simplified Method," by R. De Ponti, et al., European Heart Journal, vol. 19, Jun. 1998, pp. 943-950.

"The Puncture Needle as Guidewire: Needle Guide Technique for Percutaneous Nephrostomy," by Irvin F. Hawkins, Jr., M.D., et al., Seminars in Interventional Radiology, vol. 4, No. 2, Jun. 1987, pp. 126-130.

"PFO and Stroke: The Hidden Connection," by Paul Kramer, MD, Endovascular Today, http://www.endovasculartoday.com/02_current/10.html, printed Oct. 9, 2003.

"Teh Puncture Technique: A New Method of Transcatheter Closure of Patent Foramen Ovale," by Carlos E. Ruiz, M.D., Ph.D., et al., Catheterization and Cardiovascular Intercentions, vol. 53, 2001, pp. 369-372.

"New Transspetal Puncture Technique for Transcatheter Closure of Patent Foramen Ovale," by Robert J. Sommer, M.D., et al., Mount Sinai Medical Center, New York, New York, publication date unknown, but believed to be Jun. 2002 or ealier.

"Elastic Deployment," SMST-2000 Proceedings of the International Conference on Shape Memory and Superelastic Technologies, Apr. 30 to May 4, 2000, Asilomar Conference Center, 3 pages.

* cited by examiner

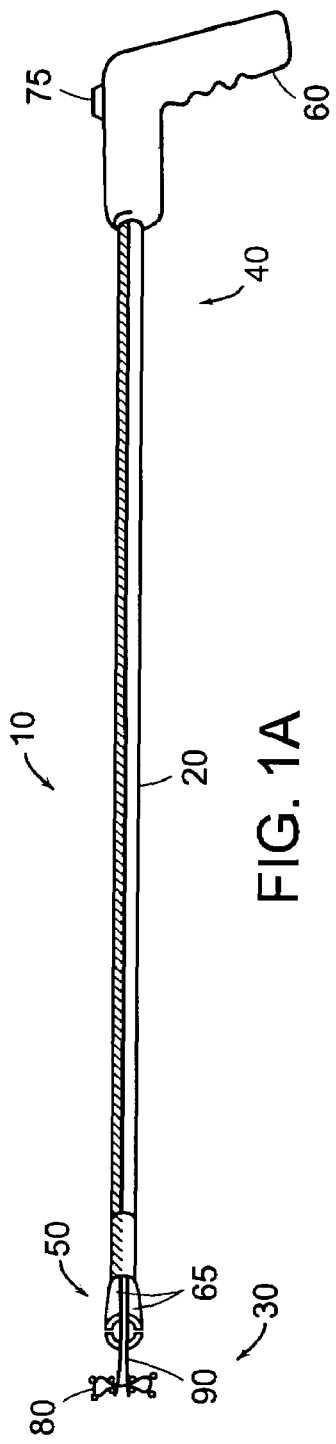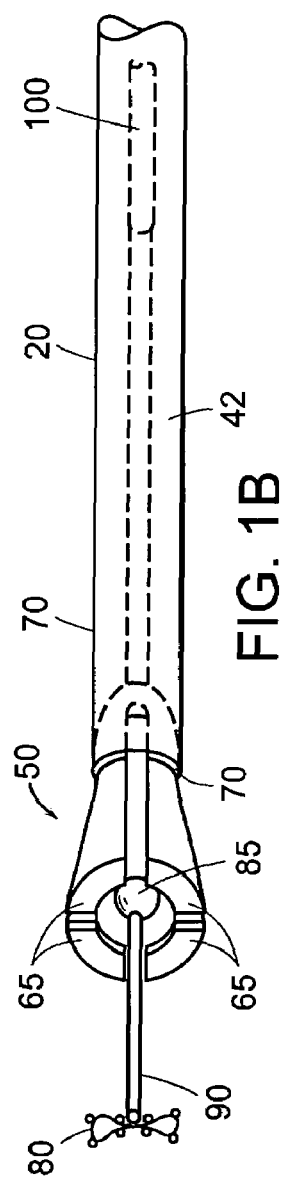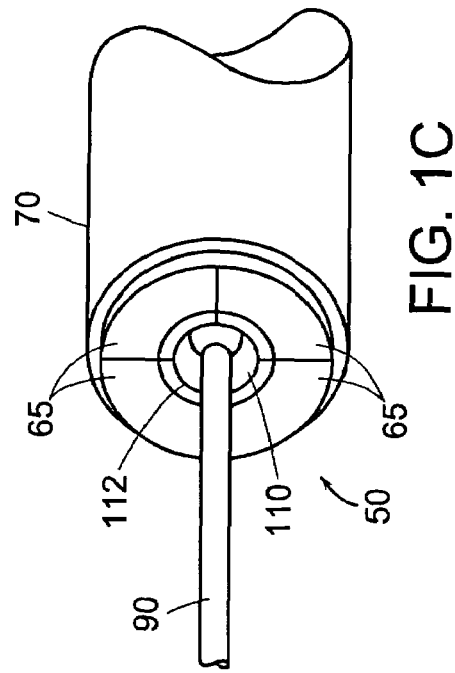

COLLET-BASED DELIVERY SYSTEM

FIELD OF THE INVENTION

This invention relates generally to a method and apparatus for delivering a medical device and more specifically to a method and apparatus for delivering a medical device percutaneously.

DESCRIPTION OF THE RELATED ART

Numerous systems for percutaneous catheter delivery of implants have been devised over the years in order to assist physicians in delivering and positioning implants within the human body in a minimally invasive manner. A classic problem with many of these percutaneous delivery systems is that the systems themselves can often adversely affect the position of the device that is being implanted. In many instances, if the delivery system is adversely influencing the positioning of the implant, the physician is forced to estimate this influential effect on implant position and take this into consideration when assessing final implant position prior to release. Further, the final released position of the implant may ultimately differ from its position when still attached to the delivery system. Additionally, any implant movement that occurs following release can adversely effect the final position. These positional deviations can in turn cause less desirable final results (such as a residual leak in the case of septal occluders or even device embolization).

Modem medical technology has produced a number of medical implants which are designed for compression into a small size tube or catheter to facilitate introduction into the vasculature. Many of these implants are subsequently expandable for either occlusion of defects or holes in the heart as well as defects along the walls of a biological passageway or blood vessel. For example a septal occluder can be used to repair a hole in the heart wall. One such occluder is described in U.S. Pat. No. 5,425,744, the entire disclosure of which is hereby incorporated by reference. While the occluder noted above is a permanent implant which, when implanted, is designed to remain in place, it can be recovered at a variety of stages during the implantation procedure. To understand the difficulty in positioning the implant some knowledge of the anatomy of the heart is required.

The human heart is divided into four compartments or chambers. The left and right atria are located in the upper portion of the heart and the left and right ventricles are located in the lower portion of the heart. The left and right atria are separated from each other by a muscular wall, the intraatrial septum, while the right and left ventricles are separated by the intraventricular septum. Either congenitally or by acquisition, abnormal openings, holes or shunts can occur between the chambers of the heart or the great vessels, causing shunting of blood through the opening. These holes or shunts may develop between the left and right atria along the intraatrial septum. Such deformities are usually congenital and result from the incomplete formation of the septum, or wall, between chambers during fetal life when the heart forms from a folded tube into a four chambered, two unit system.

These deformities can cause significant problems. Ultimately, the ill effects of these defects cause added strain on the heart which may result in heart failure if the defects are not corrected. One such defect, a patent foramen ovale (PFO), is a persistent, one-way, usually flap-like opening in the wall between the right atrium and left atrium of the heart. The PFO is the most common abnormality of fetal origin among the normal adult population. The opening between the right atrium and left atrium is formed because the embryonic left-sided septum primum is thinner than the embryonic septum secundum and overlaps the septum secundum. Since left atrial (LA) pressure is normally higher than right atrial (RA) pressure, the flap typically stays closed. Under certain conditions, however, RA pressure can exceed LA pressure creating the possibility for right to left shunting that can allow blood clots to enter the systemic circulation. This is of particular importance with patients who are prone to forming venous thrombus such as those with deep vein thrombosis or clotting abnormalities.

Transcatheter (percutaneous) closure of PFOs has become possible using a variety of mechanical closure devices, allowing patients to avoid the potential side effects often associated with standard anticoagulation therapies. These devices consist of a metallic structural framework combined with a synthetic material. The function of the material is to encourage ingrowth and encapsulation of the implant by a fibrous tissue capsule covered by a neointima. Other intracardiac defects, also currently treated with such devices, include atrial septal defects (ASDs), ventricular septal defects (VSDs), and left atrial appendages (LAAs).

The present invention, in part, addresses the issues related to these devices.

SUMMARY OF THE INVENTION

The system according to the invention combines a collet, having at least two arms which are movable between and open state and a closed state, with a flexible elongated tubular member having a first end and a second end and defining a lumen. In one position, a portion of the flexible elongated tubular member covers part of the collet collapsing the arms of the collet into its closed state to form an inner chamber. By moving the relative position between the collet and the first end of the flexible elongated tubular member, the collet extends from the flexible elongate tubular member and is self-biased to expand to its open state. The flexible elongate member is sized and shaped to fit within a blood vessel. A wire is disposed within the lumen and is attached to the collet. The wire is movable between a first position and a second position within the flexible elongate tubular member, thereby moving the collet relative to the first end of the flexible tubular member.

In one embodiment, the inner chamber of the collet is sized and configured to capture an attachment means (also referred to, herein, as an engagement means or member) of a medical device. In a further embodiment, the delivery device further includes a handle attached to the second end of the elongate member. In another embodiment, the delivery device further includes an actuator at least partially disposed in the handle for changing the relative position of the collet and the first end of the flexible tubular member. The delivery device includes a spring bias to bias the position of the first end of the flexible elongate tubular member with respect to the collet. In one aspect, the invention relates to a system which includes the delivery device described above and a septal occluder removably affixed to the engagement device.

In another aspect, the invention relates to a method for repairing a cardiac defect which includes the step of providing a delivery system including a flexible elongate tubular member being sized and shaped to fit within a vessel and having a wire disposed therethrough. The wire is movable between a first position and a second position relative to the flexible elongate tubular member. One end of the wire is attached to a collet having at least two arms movable between a first open state and a second collapsed state and forming an inner chamber when in the collapsed state. The inner chamber being sized and configured to capture an engagement member of a septal occluder. A first end of the flexible elongate tubular member surrounds a portion of the collet in a first position and is substantially retracted from the collet in a second position. The system also includes a septal occluder with an engagement member.

The steps of the method also include capturing the engagement member within the inner chamber of the collet, inserting the first end of the flexible elongate tubular member into the body of the patient and positioning the first end of the elongate member with attached septal occluder proximate to the defect. The steps of the method can further include releasing the engagement member from the collet and removing the elongate flexible member from the body of the patient.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1A is a schematic side-view of one embodiment according to the invention;

FIG. 1B is a schematic perspective view of the collet end of the embodiment of FIG. 1A in the open state;

FIG. 1C is a perspective view of the collet end of the invention in a closed state;

DETAILED DESCRIPTION

Figure 2A:
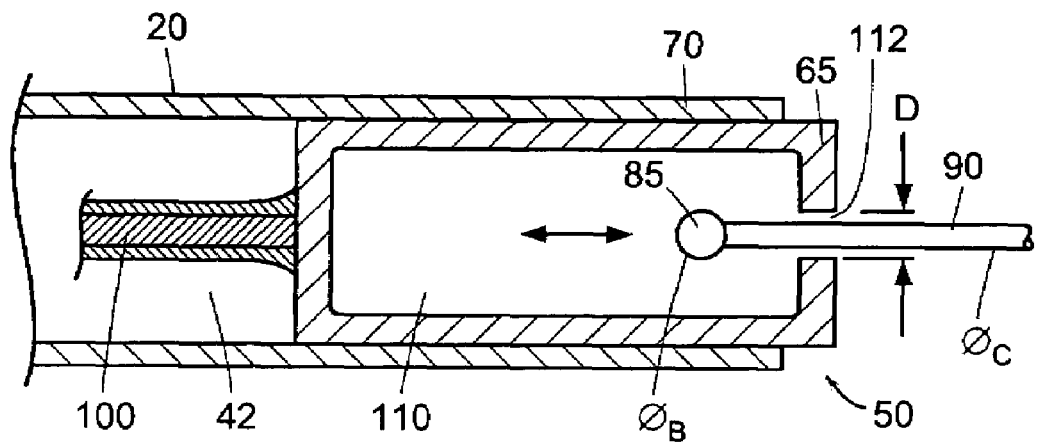
FIGS. 2A and 2B depict a cross-sectional view of the collet in a closed state holding an engagement member.

Referring to FIGS. 1A-1C, in one embodiment, the delivery system 10 of the invention includes a flexible, elongated tubular member 20 having a first end 30 and a second end 40 and defining a lumen 42. A collet 50 is located at the first end 30 and a handle 60 is attached to the second end 40. The collet 50 includes a plurality of arms 65 and is attached to a wire 100 (FIG. 1B) which passes through the lumen 42 to the handle 60. The handle 60 includes an actuator 75 at least partially disposed within the proximal handle 60 and which is connected to the wire 100. The actuator 75 moves the wire 100 toward the first end 30 and away from the first end 30 within the flexible elongated tubular member 20 thereby causing the collet 50 also to move into and out of the first end of the flexible elongated tubular member 20. The mechanism of the actuator can be any mechanism known to one skilled in the art to cause the wire 100 to move within lumen 42. It should also be noted that although the actuator is shown as a button 75 located on top of the handle 60, any position on the handle is contemplated and the actuator can take any form, such as a trigger.

Referring to FIG. 1B, the arms 65 of the collet 50 when unconstrained are normally biased to be in the open position. Referring to FIG. 1C, when the collet 50 is retracted by the wire 100 into the flexible elongated tubular member 20, the wall 70 of the flexible elongated tubular member 20 acts as a sleeve which forces the arms 65 of the collet 50 into a closed position. In the closed position, the arms 65 of the collet 50 define an inner chamber 110 having an access opening 112. The inner chamber 110 and access opening 112 are sized and shaped to accept an engagement means (also referred to, herein, as an attachment means) such as an engagement member 85 of a medical device such as a septal occluder 80.

Figure 2B:
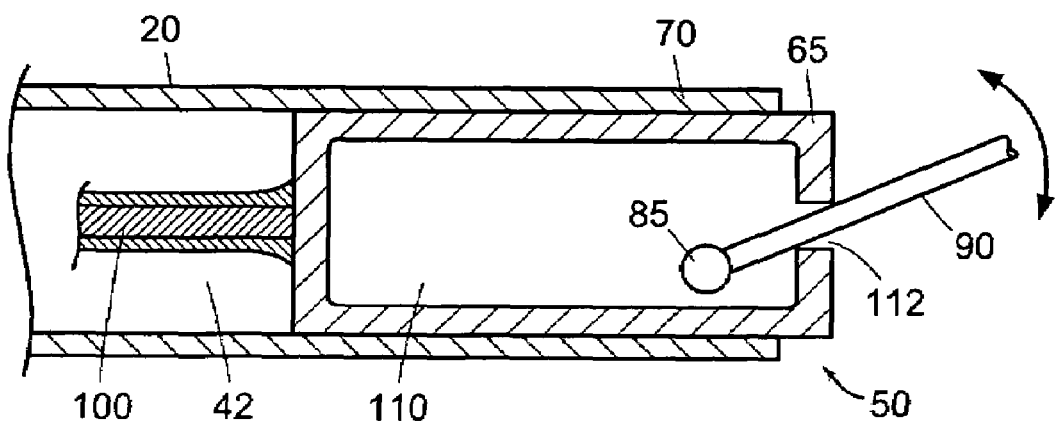
Figure 3:
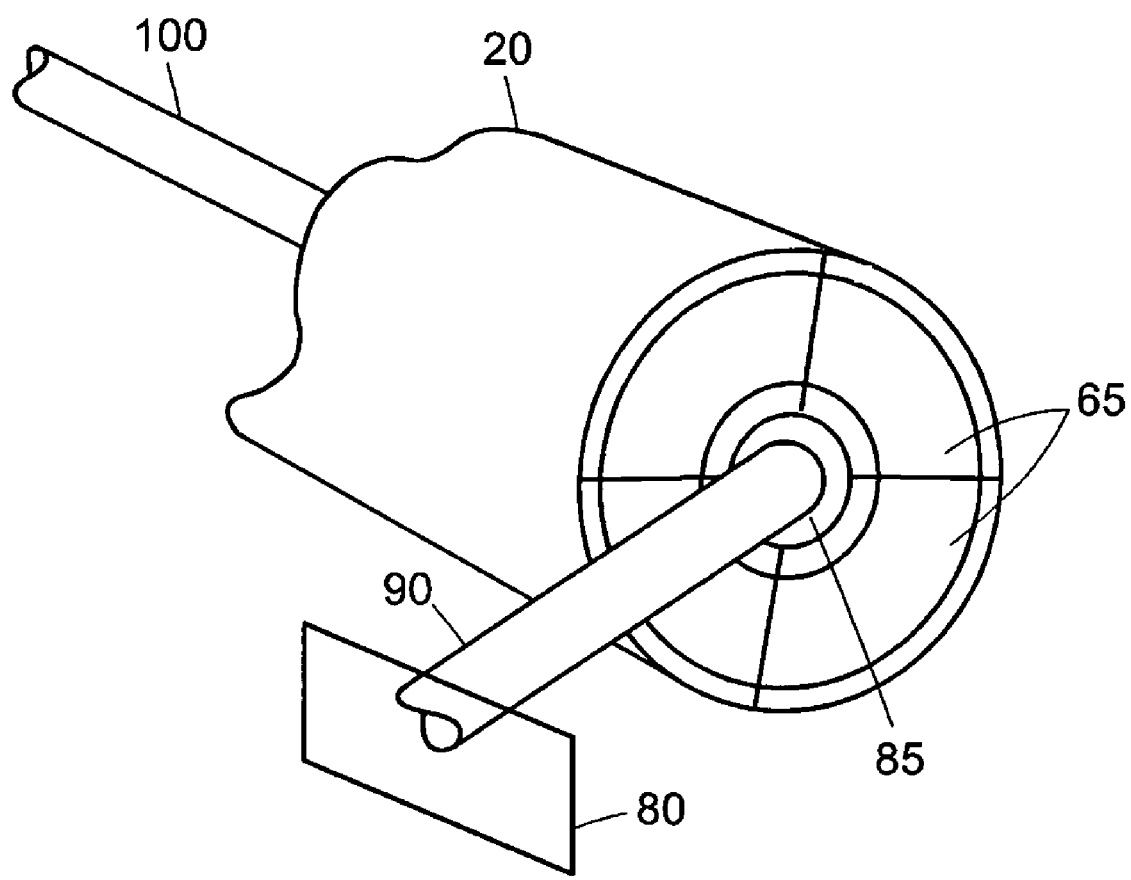
FIG. 3 is a perspective view of the collet shown in FIG. 2B with the engagement member and connector off-axis to the axis of the collet.

Referring to FIGS. 2A and 2B, the inner chamber 110 is large enough to permit the engagement means (member) 85 to move about within the chamber 110 while the access opening 112 is sufficiently small to trap the engagement means 85 and sufficiently large enough to permit the opposite end of the connecting rod 90 to move toward and away from the end of the flexible elongated tubular member 20 and about a cone of freedom of motion. This combination of chamber 100 and opening 112 permits a large degree of mobility (e.g., many degrees of freedom in translation and rotation) for the connecting rod 90 thereby reducing the constraints placed upon the orientation of the implant 80 to which the connecting rod 90 and engagement member 85 are connected as shown in FIG. 3.

Figure 4A:
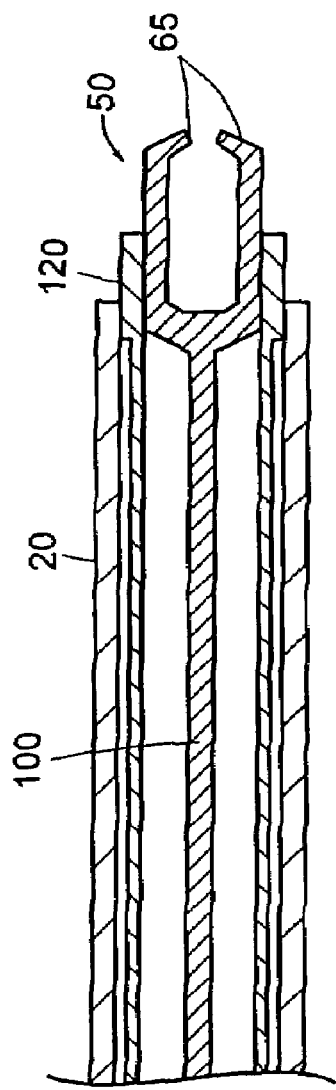
FIGS. 4A and 4B are cross-sectional view of another embodiment of invention.
Figure 4B:
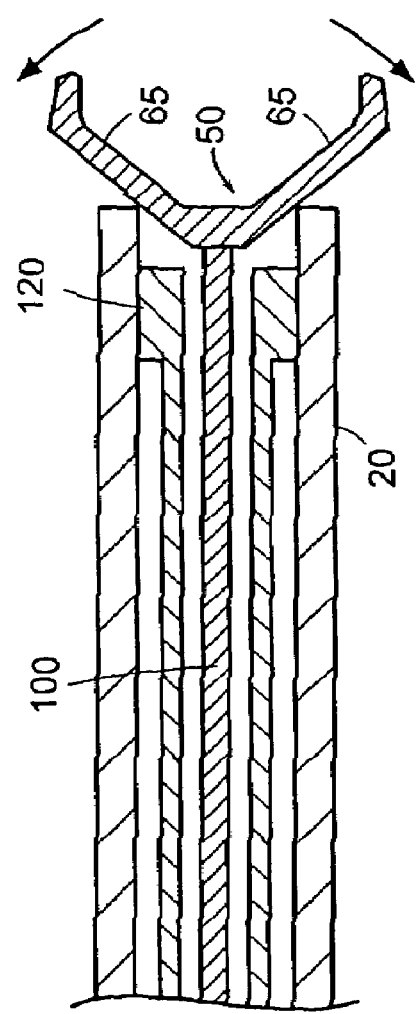

Referring to FIG. 4A, in another embodiment the elongated flexible tubular member 20 does not act as the sleeve constraining the collet 50. In this embodiment the collet 50 is held in a fixed position relative to the elongated flexible tubular member 20 by a wire 100. In this embodiment the actuator 75 does not cause the wire 100 to move the collet 50. Instead there is a movable sleeve 120 located within the lumen 42 of the elongated flexible tubular member 20 which is connected to the actuator 75. This sleeve 120 moves from a forward position shown in FIG. 4A which encloses a portion of the collet 50 causing the arms 65 to be in a closed position to a rearward position shown in FIG. 4B upon actuation of the actuator 75. When in the rearward position the movable sleeve 120 is retracted from the collet 50 thereby allowing the arms 65 of the collet 50 to open.

In operation, the engagement member 85 of the medical device 80 is held by the jaws 65 of the collet 50. The device 10 is inserted into a blood vessel of the patient and the medical device 80 is positioned at the desired spot in the body. At that point the device 80 is released. If the device 80 needs to be repositioned the jaws 65 grasp the engagement means 85 and the device 80 is moved. Once the device 80 is in the proper position, the jaws 65 are opened releasing the device 80 and the flexible, elongated, tubular member 20 is removed from the blood vessel.

While the present invention has been described in terms of certain exemplary preferred embodiments, it will be readily understood and appreciated by one of ordinary skill in the art that it is not so limited and that many additions, deletions and modifications to the preferred embodiments may be made within the scope of the invention as hereinafter claimed. Accordingly, the scope of the invention is limited only by the scope of the appended claims.

What is claimed is:

1. A delivery system for implanting an intracardiac device, said delivery system comprising:
   an intracardiac device, said intracardiac device comprising an engagement member and a connecting member;
   a delivery device, said delivery device comprising:
      a flexible elongate member comprising a lumen, said elongate member having a first end and a second end;
      a collet moveable within said lumen of said elongate member, said collet comprising a proximal end and a distal end and having at least two arms, said arms being movable between a first open state and a second closed state, at least the portion of said arms closest to said distal end of the collet form an inner chamber having an internal diameter larger than a diameter of the engagement member and comprising an opening at said distal end when in said closed state, said opening having a length smaller than the internal diameter of said inner chamber when in said closed state and an internal diameter along said length larger than a width of the connecting member and smaller than said internal diameter of the inner chamber when in said closed state; and an actuator, said actuator changing the relative position of said collet and said flexible elongate member for transitioning said collet between said closed state and said open state; and wherein said distal opening and said inner chamber of said collet, in said closed state, are sized and shaped to grasp the engagement member of said intracardiac device and to permit said connecting member of said intracardiac device to move toward and away from said distal opening and about a cone of many degrees of freedom in translation and rotation.

2. The delivery system of claim 1 wherein said delivery device further comprises a handle attached to the proximal end of said elongate member.

3. The delivery system of claim 2 wherein said actuator of said delivery device is at least partially disposed in said handle for changing the relative position of said collet and said flexible elongate member.

4. The delivery system of claim 1 wherein said collet of said delivery device comprises two arms.

5. The delivery system of claim 1 wherein said collet of said delivery device comprises three arms.

6. The delivery system of claim 1 wherein said collet of said delivery device comprises four arms.

7. The delivery system of claim 1 wherein said intracardiac device is a septal occluder.

8. The delivery system of claim 1 wherein said inner chamber of said delivery device is cylindrical in the closed state.

9. The delivery system of claim 1 wherein said connecting member of said intracardiac device is substantially cylindrical.

10. A delivery system for implanting an intracardiac device, said delivery system comprising:

an intracardiac device, said intracardiac device comprising an engagement member and a connecting member;

a delivery device, said delivery device comprising:

a flexible elongate member comprising a lumen, said elongate member having a first end and a second end;

a collet, said collet comprising a proximal end and a distal end and having at least two arms, said arms being movable between a first open state and a second closed state, at least the portion of said arms closest to said distal end of the collet form an inner chamber having an internal diameter larger than a diameter of the engagement member and comprising an opening at said distal end when in said closed state, said opening having a length smaller than the internal diameter of said inner chamber when in said closed state and an internal diameter along said length larger than a width of the connecting member and smaller than said internal diameter of the inner chamber when in said closed state;

a sleeve movable between a first position and a second position within said elongate member; and an actuator, said actuator changing the relative position of said collet and said sleeve for transitioning said collet between said closed state and said open state; and wherein said distal opening and said inner chamber of said collet, in said closed state, are sized and shaped to grasp the engagement member of said intracardiac device and to permit said connecting member of said intracardiac device to move toward and away from said distal opening and about a cone of many degrees of freedom in translation and rotation.

11. The delivery system of claim 10 wherein said intracardiac device is a septal occluder.

12. The delivery system of claim 10 wherein said connecting member of said intracardiac device is substantially cylindrical.

* * * * *